(12) United States Patent
Schaffner et al.

(10) Patent No.: US 7,425,130 B2
(45) Date of Patent: Sep. 16, 2008

(54) DENTAL WEDGES

(76) Inventors: Alfred Schaffner, Strada Cantonale, CH-6805 Mezzovico (CH); Richard Goldman, 8 Thatch Pond Rd., Smithtown, NY (US) 11787

( * ) Notice: Subject to any disclaimer, the term of this patent is extended or adjusted under 35 U.S.C. 154(b) by 107 days.

(21) Appl. No.: 11/125,358

(22) Filed: May 9, 2005

(65) Prior Publication Data
US 2005/0272005 A1    Dec. 8, 2005

(30) Foreign Application Priority Data
May 8, 2004    (DE) ................ 10 2004 022 778

(51) Int. Cl.
*A61C 7/00*    (2006.01)
(52) U.S. Cl. .................................... 433/149
(58) Field of Classification Search ............... 433/39, 433/40, 149
See application file for complete search history.

(56) References Cited

U.S. PATENT DOCUMENTS

| | | |
|---|---|---|
| 3,510,948 A | 5/1970 | Walthall |
| 3,636,631 A | 1/1972 | Tofflemire |
| 3,815,243 A | 6/1974 | Eames |
| 3,890,714 A | 6/1975 | Gores |
| 4,337,041 A | 6/1982 | Harsany |
| 4,631,030 A | 12/1986 | von Weisenfluh |
| 5,743,738 A | 4/1998 | Baffelli et al. |
| 5,890,900 A * | 4/1999 | Fischer et al. ............... 433/149 |
| 6,142,781 A | 11/2000 | Fisher |
| 6,375,463 B1 * | 4/2002 | McLean et al. ............. 433/149 |
| 6,402,514 B1 * | 6/2002 | Fischer et al. ............... 433/149 |
| 2004/0014006 A1 * | 1/2004 | Garrison et al. ............. 433/149 |

FOREIGN PATENT DOCUMENTS

| | | |
|---|---|---|
| CH | 669514 | 2/1986 |
| DE | 10119733 | 10/2002 |
| EP | 0169803 | 6/1985 |

(Continued)

OTHER PUBLICATIONS

Kerrhawe Katalog 2002 pp. 19-21 Commonsense Dental Products, Flex Wedge, Website 4 pages.

(Continued)

*Primary Examiner*—Ralph Lewis
(74) *Attorney, Agent, or Firm*—Horst M. Kasper

(57) ABSTRACT

A dental wedge for use in a dental medical treatment and restoration of hollow spaces associated with caries between neighboring teeth. The dental wedge has a triangular cross-section and a free end running out to a rounded tip. The dental wedge (1) is bent upwardly like a saber. The base face (3) and the side faces (4) of the dental wedge (1) are arched concavely inwardly. The impact edges (5) of the base face (3) and of the side faces (4) of the dental wedge (1) are rounded. The dental wedge (1) exhibits a first, longer wedge section (1a) and a second, shorter wedge section (1b), wherein the impact edges (5) between the base face (3) and the side faces (4) in the first wedge section (1a) are running parallel to each other. The impact edges (5) in the second wedge section (1b) run toward each other toward the free upwardly bent tip (2) of the dental wedge (1).

20 Claims, 5 Drawing Sheets

FOREIGN PATENT DOCUMENTS

| | | |
|---|---|---|
| EP | 0668060 | 2/1995 |
| EP | 0860149 | 2/1997 |
| EP | 1192915 | 4/2002 |
| WO | WO0217813 | 3/2002 |

OTHER PUBLICATIONS

Garrison Dental Solutions Inc., Features and benefits of the WedgeWand, Website, 2 pages.

Polydentia SA, Solution by Alwicom SA, Website 2 pages.

* cited by examiner

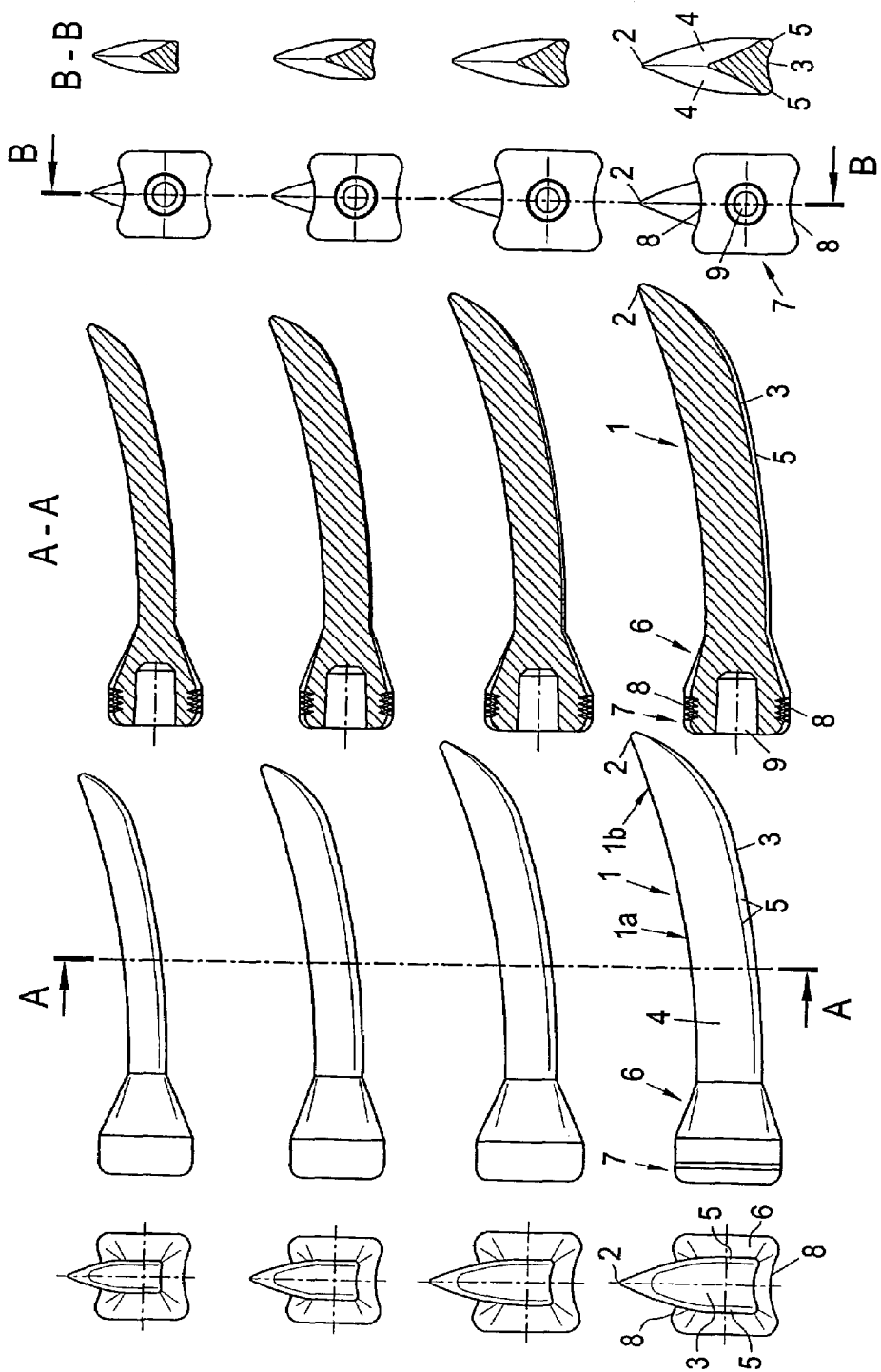

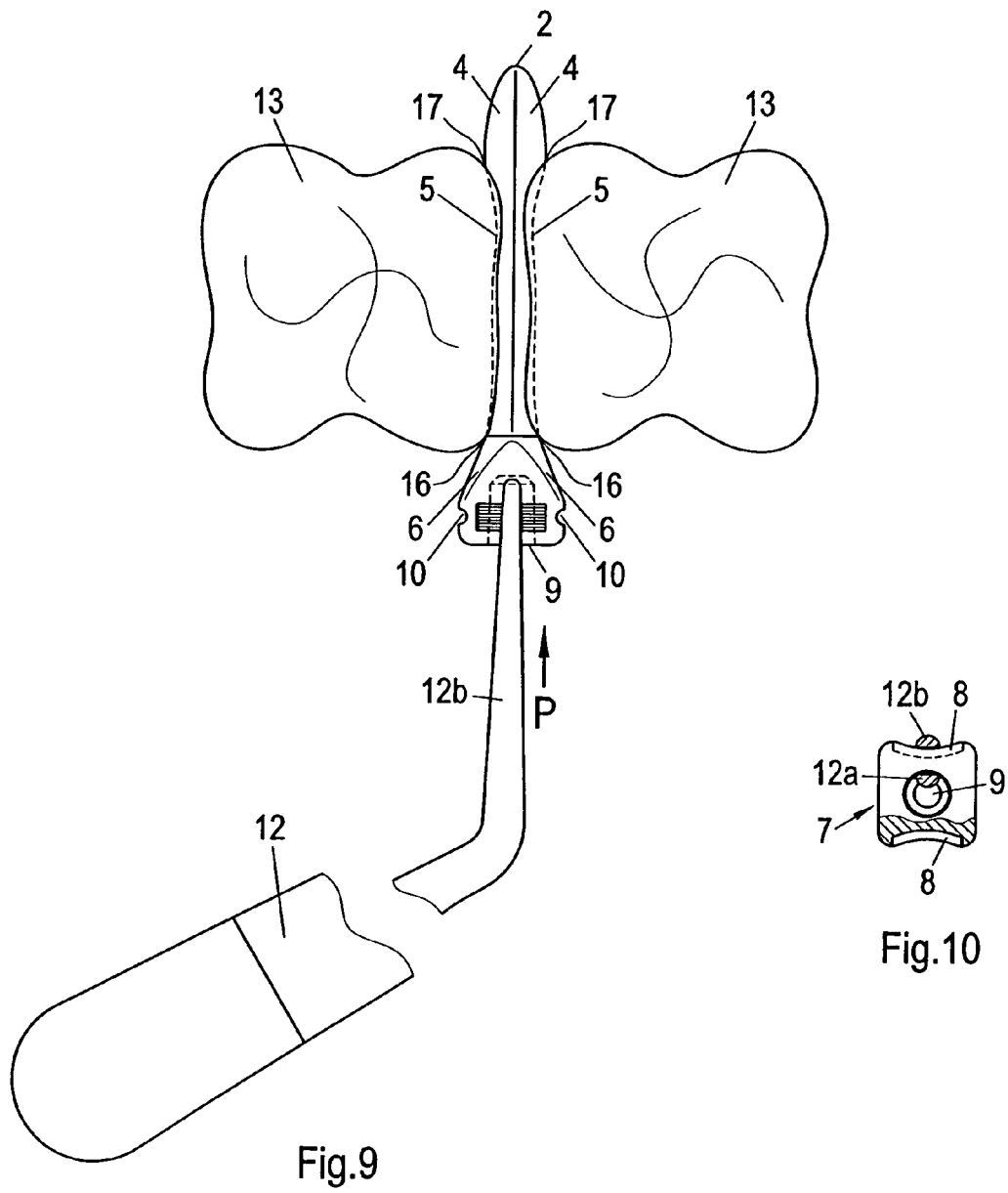

DENTAL WEDGES

BACKGROUND OF THE INVENTION

1. Field of the Invention

The Invention relates to dental wedges to be employed in connection with dental medical treatment and restoration of hollow spaces between neighboring teeth associated with caries.

2. Brief Description of the Background of the Invention Including Prior Art

If the part of a tooth is to be restored, which part contacted a neighboring tooth prior to affection with caries, then it is required to delimit hand to support the filling material during the entering into the hollow space and during the following hardening such that the filling material can adapt exactly to the healthy part of the tooth. It is usual for this purpose to place a matrix band around the tooth to be treated and to pull fast, such that the matrix band can so to speak replace the destroyed part of the tooth wall during treatment. For the matrix band to fulfill its function, the matrix band has to be approached as far possible to the shape of the tooth and has to be fixed in the position such that the filling material brought in finally corresponds to the outer face of the healthy tooth and does not protrude and where recesses can form, which recesses favor anew the formation of caries. A dental wedge is pressed between the neighboring teeth and the gums for this purpose, wherein the dental wedge presses and wedges the matrix band against the tooth to be treated and simultaneously also presses the teeth somewhat apart. It is therewith accomplished that, if after finished treatment the matrix band is again removed, the teeth can support again each other mutually by returning into their starting position and the space previously claimed by the matrix band does not remain as a gap or as a slot opening.

Typically, dental wedges have a conical, long extended shape and a triangular or also V-shaped cross-section. The dental wedge has to be absolutely immovable in its position between two teeth during a tooth treatment and therefore has to be pressed with a force, usually generated with the aid of a special instrument, between the teeth, until the dental wedge is maintained in position between the two teeth based on friction. The dental wedges are offered also in different sizes such that the selection can be made corresponding to the respective anatomy.

The U.S. Pat. No. 6,074,210 describes dental wedges, wherein the side view of the dental wedges is comparable to a long extended, pointed converging triangle and the wherein the cross-section of the dental wedges resembles a turned over V, that is downwardly open, that is where the dental wedge comes to touch with the interdental papilla. By providing in this manner the larger elasticity to the side walls, the introduction of the dental wedges between two teeth is to be alleviated, the support of the dental wedges between the two teeth is improved and an adaptation as exact as possible to the form of the teeth, also at cavities, as well as the restoration after the removal at the end of the treatment is achieved. The side faces are to be structured by being furnished with a corrugation or with notches. This is to increase again the support of the side faces between the teeth. The dental wedges exhibit a dice shaped prolongation at their broad end disposed remote from the tip, wherein the dental wedges can be gripped at the dice shape prolongation with a suitable instrument, for example a forceps and can be pressed with a sufficient force between two teeth in order to find the required support. The two lower longitudinal edges are obtusely angled off at about half their length, whereby a better adaptation to the anatomy of a patient is to be accomplished.

It is a disadvantage of these dental wedges that the wedge effect is decreased based on the downwardly open shape. Corrugations or notches at the side faces are acting opposingly to an optimal adaptation to the anatomic situation different in each treatment case. It is also perceived to be disadvantageous that a particular forceps is required for the introduction of these dental wedges.

This latter recited disadvantage is avoided according to the U.S. patent application Ser. No. 004/0014006 A1, where it is taught to furnish each dental wedge through a constriction or necking with a formed on actuating rod, that is the two parts are formed as a single part. The rod can as desired be angled off or bent off at the constriction or necking for the actuating. The actuating rod is broken off and thrown away after the pressing in of the dental wedge into the interdental space. This means a tremendous waste of material; the actuating rod has to be formed comparatively long and also forceful in comparison with the proper dental wedge such that the required force can be exerted onto the dental wedge with the actuating rod during pressing in. It can prove to be a disadvantage that the actuating rod can be angled off or bent off at the constriction, since the force vector in push direction is thereby reduced.

The dental wedge itself comprises two sections with a different cross-sectional shape. The cross-section of the first, front section has the shape of a triangle, wherein the side faces are arched concavely inwardly and run toward each other in a longitudinal direction toward a rounded off tip and wherein the tip is bent upwardly. The wedge transitions into a section with trapezoidal cross-section at the end of the first, front section disposed remote from the tip. This section with trapezoidal cross-section is to spread additionally the teeth upon introduction into an interdentium. Furthermore thereto joins still a preferably cuboid shaped prolongation, also set off by a constriction, wherein the above recited actuating rod is formed finally at the cuboid shape prolongation. The wedge can, after the treatment of the teeth, be gripped with a forceps and removed after a prior breaking off of the actuating rod. This means that also according to this proposal of a dental wedge with formed on, but breakable off actuating rod, the dentist finally cannot get along without a further instrument, and the further instrument necessary is the recited prolongation as a connection piece between the proper dental wedge and the actuating rod. The overall shape with the different sections and parts becomes therewith complicated and expensive in production.

SUMMARY OF THE INVENTION

1. Purposes of the Invention

It is an object of the present Invention furnish a dental wedge, which wedge is still better formed anatomically, but nevertheless has a simpler form and each dental wedge is non-complicated in the production as far as possible and wherein the dental wedge can be introduced into the interdentium but with a force required for secure support and in a simple way with a simple instrument, which nevertheless is at hand with a dentist, preferably with a forceps tweezer. The dental wedge is to be adapted as optimal as possible to each possible dental shape, to cavities present and for example also to subgingival filling and inlay edges under careful and gentle treatment of the dental papilla.

These and other objects and advantages of the present invention will become evident from the description which follows.

2. Brief Description of the Invention

According to the present Invention this is achieved by transitioning the dental wedge at its end disposed relative remote to the tip into a truncated cone shape or truncated pyramid shape widening end piece, wherein engagement faces for a forceps tweezers or other suitable dental gripping instrument are formed in the widening end piece.

By dispensing in this manner of particular prolongations, at which the dental wedge can be captured, the dental wedge obtains a relatively simple overall shape, wherein the simple overall shape acts lowering the costs of production and of the materials employed. At the same time the overall shape distinguishes by a simple handling, wherein the treating dentist is able to capture securely and fast the dental wedge at the provided engagement faces and can exactly place the dental wedge with an instrument which is anyway at hand with the dentist.

A particularly advantageous embodiment of the dental wedge exhibits in addition the following features in combination:

i. The edge is bent upward like a saber,
ii. The base face and the side faces of the edge are arched concavely inwardly,
iii. The impact edges of the base face and of the side faces of the dental wedge are rounded,
iv. The wedge exhibits a first, longer wedge section and a second, shorter wedge section, wherein the impact edges between the base face and the side faces are running parallel to each other in the first wedge section and run only in the second wedge section toward each other to the free, upwardly bent tip of the dental wedge.

The dental wedge obtains in this manner an anatomically best adapted shape, which shape covers all requirements which can be presented to a dental wedge. The dental wedge can exactly be placed between two neighboring teeth and the dental wedge adapts itself there optimally to the shape of the teeth also in the region of cavities and here nevertheless an optimum wedge effect is obtained. The gingival papilla at the exit point of the dental wedge is treated with care as far as possible by the saber shaped bending up of the tip of the dental wedge. The conically arched base face adapts and conforms gently to the gingival papilla and furnishes in addition to a good wedge effect also a high restoring capability of the wedge, in case the wedge is taken out again after finishing of the treatment. An optimum wedging is achieved both at the entry point as well as at the exit point at the interdentium based on the parallel disposition of the impact edges between the base face and the side faces in the region of the first, longer wedge section.

According to one embodiment of the Invention, a bore hole in is entered into the end piece for forming of engagement faces for the forceps tweezers or another dental gripper instrument.

Advantageously, a cuboid shape pedestal joins to the end piece, wherein the cuboid shape pedestal is also penetrated by a bore hole.

Preferably the bore hole is performed as an axial pocket bore hole and at least one lateral face of the pedestal is arched concavely inwardly as a second engagement face for a forceps tweezers or another gripping instrument. If one tweezer arm engages at the inner face of the bore hole and if the second tweezer arm engages at the lateral face of the pedestal, then an effectively high, axially directed pressure can be obtained during pressing in of the dental wedge into the interdentium and the required wedge effect can be achieved.

In addition the zone of contacts for the gripper arm, or arm of tweezers at the lateral face of the pedestal can be grooved or corrugated for better and more secure gripping.

According to a further embodiment the bore hole is performed as a passing through cross bore hole and offers the zone of contact for the first gripper arm or arm of tweezers; the zone of contact for the second gripper arm or arm of tweezers is then preferably formed at the basis face of the end piece or pedestal. The required high pressure during pressing in of the dental wedge can be exerted also with this formation of the zone of contact.

According to a further embodiment of the Invention additionally or alternatively indentations are formed as zones of contact for an arm of tweezers or gripper arm in at least two lateral faces disposed opposite to each other.

Where the impact edges between the base face and the side faces of the dental wedge are sloped slightly toward the inside, then one obtains a very good adaptation also at sub gingival filling edges.

The base face of the wedge can be furnished with a light reflecting structuring, preferably of the kind of a red reflex reflector such that the light is optimally reflected in a direction onto a matrix band placed around the tooth to be treated.

The novel features which are considered as characteristic for the invention are set forth in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

The Invention is described in more detail and by way of example in the following by way of the attached drawings; there is shown in:

FIG. 1 a front elevational view with view direction onto the wedge tip of a dental wedge according to the present Invention in four different sizes, FIG. 2 a side elevational view with view direction onto the wedge tip of a dental wedge according to the present Invention in four different sizes, FIG. 3 a longitudinal sectional view with view direction onto the wedge tip of a dental wedge according to the present Invention in four different sizes, FIG. 4 a rear view with the view direction onto the wedge tip of a dental wedge according to the present Invention in four different sizes, FIG. 5 a sectional view along the section line A-A of FIG. 2 with view direction onto the wedge tip of a dental wedge according to the present Invention cross-sectioned in four different sizes, FIG. 6 a longitudinal sectional view through two neighboring teeth with a dental wedge introduced into the interdentium, FIG. 7 a perspective view onto the interdental face of a resting dental wedge, FIG. 8 a cross sectional view through two neighboring teeth with pressed in dental wedge, FIG. 9 a top planar view onto two neighboring teeth with pressed in dental wedge and the handling of the dental wedge, FIG. 10 a perspective view onto the dental wedge in the direction of the arrow P of FIG. 9, and FIG. 11 a substantially enlarged part of a longitudinal section through two neighboring teeth with pressed in dental wedge.

DESCRIPTION OF INVENTION AND PREFERRED EMBODIMENT

Figure 6:
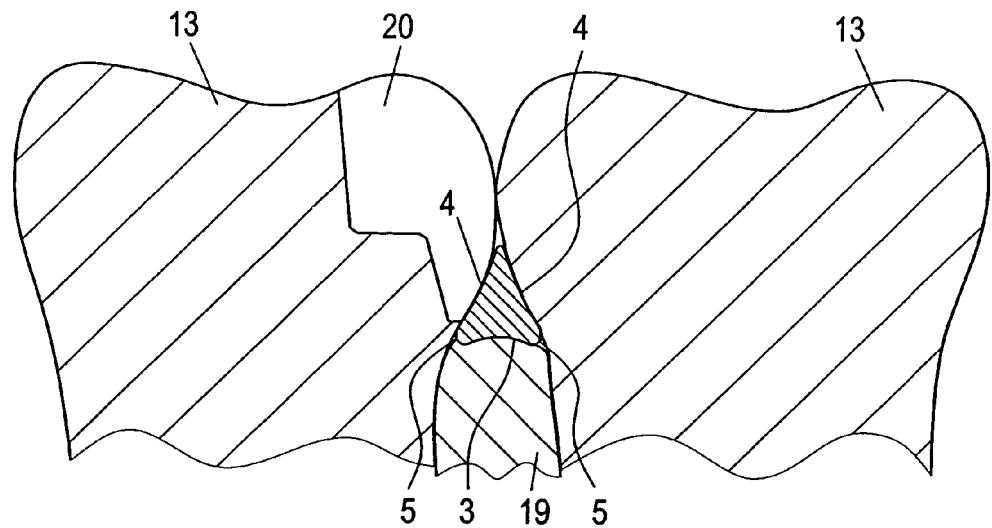

The FIGS. 1 to 5 show the dental wedge in four different sizes, however otherwise of identical construction and in each case of five different views. The proper dental wedge 1 accordingly is upwardly bent like a saber (compare FIGS. 1 through 3) and exhibits here a first, longer wedge section 1a and a second, shorter wedge section 1b, wherein the second shorter wedge section 1b runs out at its free end to a preferably rounded, upwardly directed tip 2. The wedge 1 has a triangular cross-section (compare FIG. 5), wherein both the base face 3 as well as the exterior side faces 4 are arched concavely. The impact edges 5 of the base face 3 and of the two exterior side faces 4 are preferably also rounded off. The impact edges 5 are running parallel to each other in the first wedge section 1a and only in the second wedge section 1b the impact edges 5 run towards each other to the tip 2. The wedge 1 transitions into a truncated cone shaped widening end piece 6 or, as illustrated, a truncated pyramidal shaped widening end piece 6, and a cuboid shape pedestal 7 can join in the widening end piece 6. In addition, the lateral faces of the pedestal 7 or preferably the upper lateral face 8 and the lower lateral face 8 disposed opposite to each other can be arched concavely inwardly (compare FIGS. 1 and 4) and can additionally be grooved and/or corrugated (compare FIG. 3). The pocket bore hole 9 is entered from the free end of the pedestal 7 into the pedestal 7 and reaching up to the end piece 6. Alternatively or additionally to the pocket bore hole 9, indentations 10 can be furnished at two oppositely disposed lateral faces 8 of the pedestal 7, wherein the indentations 10 can be grooved or corrugated for their respective purpose (compare further down). As illustrated in FIG. 9, it is the purpose of both the pocket bore hole 9 together with one of the concavely inwardly arched lateral faces 8 of the pedestal 7 (compare for this purpose also FIG. 10) as well as also, alternatively, of the indentations 10, to furnish the possibility to capture the dental wedge with forceps tweezers 12 and to push and to press in the dental wedge into the interdentium between two neighboring teeth 13 in order to press a matrix band (not illustrated) on there closely adapted to the shape of the teeth 13 and to spread thereby the teeth 13 by a certain measure. If as illustrated in FIGS. 9 and 10 the one arm 12 of tweezers grips into the bore hole 9 and the other arm 12b of tweezers grips at one of the concavely arched lateral faces 8, then a very high pressure can be exerted during insertion of the dental wedge in axial direction, wherein the very high pressure very much alleviates and renders secure the introduction and exact placing in an immovable position (as well as later also the removal with pulling) of the dental wedge.

Figure 8:
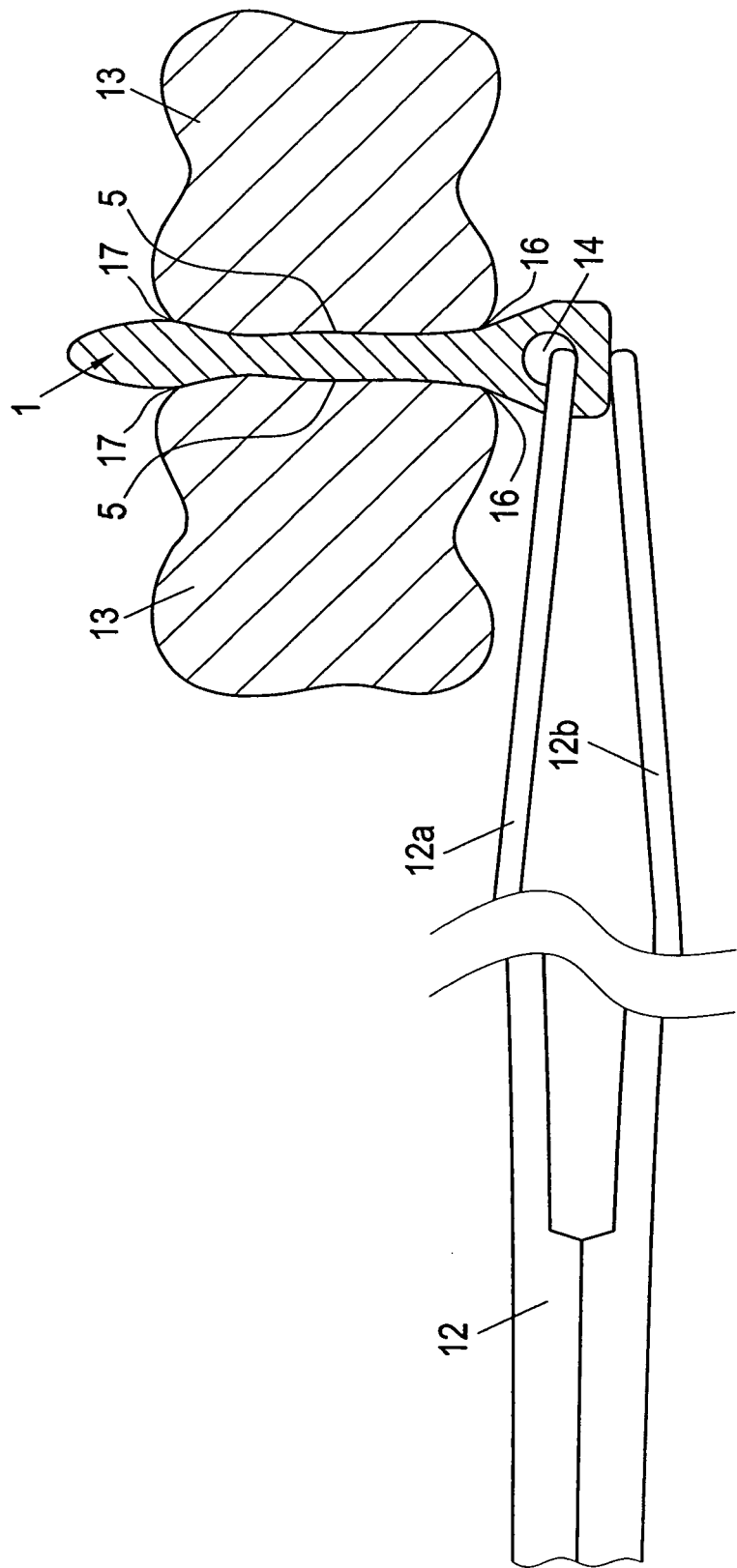

FIG. 8 shows a variation of the support possibility during introduction and removal of the dental wedge. A passing through cross bore hole 14 is furnished here in the region of the expanding end piece 6 and of the pedestal 7, wherein one of the arms 12a of the tweezers can grip into the passing through cross bore hole 14, while the other arm 12b of the tweezers captures the pedestal 7 at its basis face 15. Also in this fashion a sufficient high pressure can be exerted in axial direction of the dental wedge in order to press the dental wedge firmly between the teeth 13.

The dental wedge according to FIG. 8 can have a first wedge section 1a and a second wedge section 1b similar to that shown in FIGS. 1 to 5. Also the pedestal 7 can be formed like that of FIGS. 1 to 5 with the exception that no pocket bore hole 9 is present. An axis of the cross bore hole 14 can be located in a plane defined by the dental wedge 1. An outer diameter of the pedestal 7 can be from about 1 to 1.5 times the diameter of the cross bore hole 14. A distance of the cross bore hole periphery to the free end of the pedestal can be from about 0.4 to 0.6 times the diameter of the cross bore hole 14. A distance of a lateral face 8 of the pedestal 7 can be from about 0.5 to 0.7 times the diameter of the cross bore hole 14.

It can also be clearly recognized in FIGS. 8 and 9 how the dental wedge 1 anatomically particularly well be inserted in the interdentium and optimally be adapted to the shape of the two neighboring teeth 13 and also that the entry point 16 and that the exit point 17 is optimally wedged; also tapers and recesses at the neck of the tooth are captured optimally.

Figure 7:
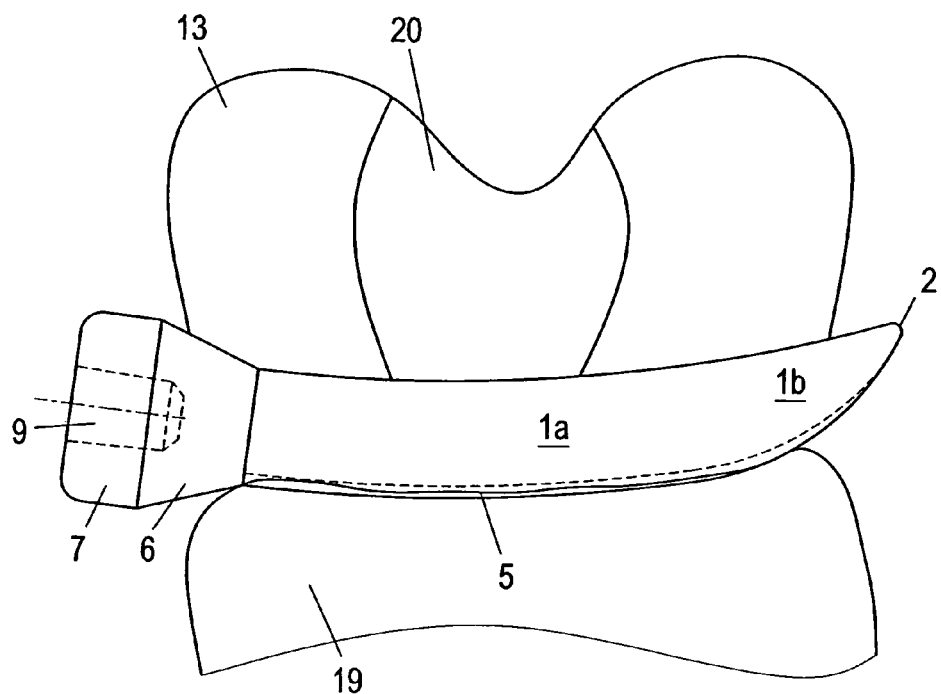

It becomes clear from the side elevational view of FIG. 6 how the dental wedge 1 with its concavely inwardly arched basis face 3 gently adapts to and conforms to the gingival papilla 19. A perfect adaptation is accomplished also in the region of the cavities 20 and a nevertheless good wedge effect is achieved based on the parallel disposition of the impact edges 5. The shape of the base face 3 results in a high restoring and release capability of the dental wedge 1 as a further advantage, in case the dental wedge 1 is again removed after finished treatment of the tooth. The two impact edges 5 are preferably in each case furnished with a sloping chamfer 21 (compare also FIG. 11), these sloping chamfers 21 take care of a good adaptation of a matrix band (not illustrated) placed around the tooth for the treatment even in case of sub gingival, that is under the gingival margin disposed, filling edges or inlay edges. It can be also recognized in the view of FIG. 7 how an arched wedge shape gently adapts to and conforms to the gingival papilla 19 and how the edges of the cavities are optimally wedged interdentally.

The dental wedge is produced out of a thermoplastic and preferably transparent plastic or elastomeric plastic and advantageously can exhibit overall or partially, for example at the end piece 6 with pedestal 7, a slight covering as color coding for the different wedge sizes (compare FIGS. 1 to 5). The elastomeric plastic can be poly vinyl chloride, polyethylene, polypropylene or polyurethane. The base face 3 of the dental wedge 1 can preferably be furnished with a structuring, for example in the kind of a red reflex reflector for example by way of a treatment with spark erosion or electrical discharge machining, wherein the structuring as indicated with arrows in FIG. 11 takes care of an optimum reflection of the light for example on and through a matrix band, preferably also transparent, placed around the tooth to be treated and thereby renders the work more comfortable for the dentist.

The length of the first section 1a can be from about 1.5 to 3 times the length of the second section 1b and is preferably from about 2 to 2.5 times the length of the second section 1b. the first section 1a and the second section 1b are continuous in the curvature on the side where the two side faces 4 abut. The abutting side faces 4 show substantially the same curvature as does the base face in the first wedge section 1a (FIG. 3). The radius of curvature of the base face 3 in the area of the second section 1b is from about 0.2 to 0.5 times the radius of curvature of the base face 3 in the area of the first section 1a (FIGS. 2 and 3). The transition from the first wedge section 1a to the second wedge section 1b is defined by a substantial change in the radius of curvature of the base face 3. The length of the first wedge section 1a is from about 2 to 4 times the length of the pedestal 7 and preferably from about 2.5 to 3 times the length of the pedestal 7. The radius of curvature of the dental wedge can be from about 4 to 10 times the length of the first wedge section 1a and is preferably from about 5 to 7 times the length of the first wedge section 1a.

The pedestal 7 preferably surrounds the end of the dental wedge. The pedestal 7 can have a substantially rectangular periphery as illustrated in FIG. 4. The length of the first section 1a can be from 3 to 10 times the open diameter of the bore hole 9 and is preferably from about 4 to 6 times the open diameter of the bore hole 9.

The length of the first section 1a can be from 2 to 8 times the depth of the bore hole 9 and is preferably from about 3 to 5 times the depth of the bore hole 9. The bore hole 9 can have the shape of a round cylinder with or without a threading. The bore hole 9 can have the shape of a hexagonal cylinder, of a pentagonal cylinder, of a square cylinder or of a triangular cylinder.

The width of a side face 4 in the first wedge section 1a can be from about 0.7 to 2 times the width of the base face 3 and is preferably from about 1.0 to 1.5 times the width of the base face 3.

Figure 11:
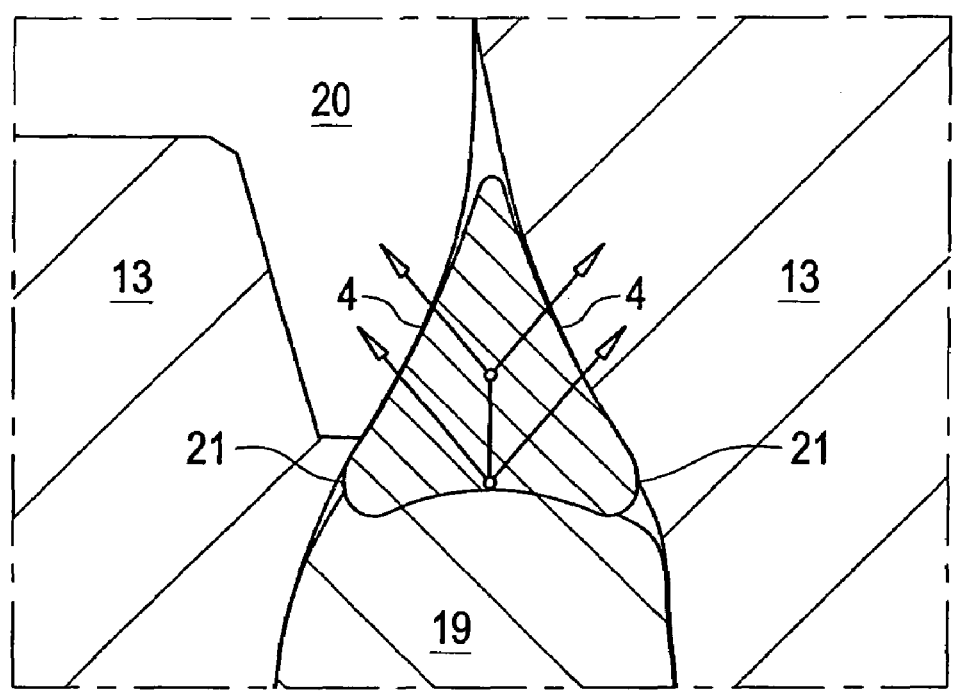

The impact edges 5 can have a radius of curvature from about 0.05 to 0.3 times the width of the base face 3 and is preferably from about 0.1 to 0.15 times the width of the base face 3. The radius of curvature of the base face 3 in a plane perpendicular to a longitudinal direction can be from about 0.8 to 1.5 times the width of the base face 3 and is preferably from about 1 to 1.2 times the width of the base face 3 (FIG. 11).

It will be understood that each of the elements described above, or two or more together, may also find a useful application in other types of medical processes and restoration procedures differing from the types described above.

While the invention has been illustrated and described as embodied in the context of a dental wedge, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

LIST OF REFERENCE NUMERALS 1 dental wedge
1a first wedge section
1b second wedge section
2 tip
3 base face
4 side face (wedge)
5 impact edges
6 end piece
7 pedestal
8 lateral faces (pedestal)
9 pocket bore hole
10 indentations
11 --
12 forceps tweezer
12a, 12b tweezer arms
13 teeth
14 cross bore hole
15 basis face
16 entry point
17 exit point
tapers and recesses
19 dental papilla
20 cavity
21 sloping chamfer

The invention claimed is:

1. A dental wedge for use in a dental medical treatment and restoration of hollow spaces associated with caries between neighboring teeth comprising
a wedge shaped section having a triangular cross-section and forming a free end of a dental wedge, with rounded impact edges of a base face and of side faces and with the free end running out to a rounded tip;
a truncated cone shaped or truncated pyramidal shaped expanding end piece (6) forming a head of the dental wedge, wherein the wedge shaped section and the head are solidly attached to each other;
wherein the expanding end piece (6) expands from a small diameter end which is connected to the wedge shaped section to a larger diameter flat end face,
a pocket recess (9) formed in the larger diameter flat end face of the expanding end piece (6) and aligned with a longitudinal axis of the wedge shaped section, wherein the pocket recess (9) serves for capturing the dental wedge with a gripping instrument, wherein the gripping instrument engages into internal faces of the pocket recess.

2. The dental wedge according to claim 1 wherein the pocket recess (9) is brought into the end piece (6), wherein the pocket recess (9) serves for capturing the dental wedge with forceps tweezers (12) or with another dental gripping instrument.

3. The dental wedge according to claim 2, wherein a cuboid shaped pedestal (7) joins to the larger diameter flat end face of the expanding end piece (6) and wherein the pedestal (7) is also penetrated by the pocket recess (9).

4. The dental wedge according to claim 2, wherein the pocket recess is performed as an axial pocket bore hole (9).

5. The dental wedge according to claim 1, wherein a cuboid shaped pedestal (7) joins to the larger diameter flat end face of the expanding end piece (6), wherein indentations (10) are formed in at least two oppositely disposed lateral faces (8) of the cuboid shaped pedestal (7).

6. The dental wedge according to claim 1, wherein the impact edges (5) between the base face (3) and the side faces (4) of the dental wedge are sloped (21).

7. The dental wedge according to claim 1, wherein the base face (3) of the dental wedge (1) is furnished with a light reflecting structuring.

8. The dental wedge according to claim 1, wherein the base face (3) of the dental wedge (1) is furnished with a light reflecting structuring of the kind of a red reflex reflector.

9. The dental wedge according to claim 1, wherein the dental wedge (1) is formed out of a thermoplastic transparent plastic.

10. The dental wedge according to claim 9, wherein the dental wedge is partly or completely furnished with a slight inking or tinting serving as a color coding for different sizes of dental wedges.

11. A dental wedge comprising
a rounded tip (2);
a second wedge section (1b) having a first end adjoining and running out to the rounded tip (2) and having a second end and having a substantially triangular cross section;
a base face (3) arched concavely inwardly;
a first side face (4) arched concavely inwardly;
a second side face (4) arched concavely inwardly, wherein the base face (3), the first side face (4) and the second side face (4) form a first wedge section (1a);
a first rounded impact edge (5) formed at a common edge of the base face (3) and the first side face (4);

a second rounded impact edge (5) formed at a common edge of the base face (3) and the second side face (4);

wherein the first wedge section (1a) has a first end adjoining the second end of the second wedge section (1b) and has a second end, wherein the first wedge section (1a) is bent upwardly like a saber;

wherein the first wedge section (1a) is longer and wherein the second wedge section (1b) is shorter, wherein the first rounded impact edge (5) and the second rounded impact edge (5) between the base face (3) and the side faces (4) in the first wedge section (1a) are running parallel to each other and wherein impact edges (5) in the second wedge section (1b) run toward each other toward the free upwardly bent rounded tip (2) of the dental wedge (1), wherein the dental wedge (1) transitions at its end disposed remote from the tip (2) into a truncated cone shaped or truncated pyramid shaped widening end piece (6), wherein the widening end piece (6) expands from a small diameter end which is connected to the second end of the first wedge section (1a) to a larger diameter flat end face, a pedestal (7) having a first end adjoining the larger diameter flat end face and having a second end;

a pocket recess (9) formed in the second end of the pedestal (7) and extending into the widening end piece (6) and aligned with a longitudinal axis of the first wedge section, wherein the pocket recess (9) serves for capturing the dental wedge with a gripping instrument, wherein the gripping instrument engages into internal faces of the pocket recess.

12. A dental wedge for use in a dental medical treatment and restoration of hollow spaces associated with caries between neighboring teeth with a triangular cross-section, with rounded impact edges of the base face and of the side faces and with a free end running out to a rounded tip, wherein a dental wedge (1) transitions at an end of the dental wedge disposed remote from the tip (2) into a truncated cone shaped or truncated pyramidal shaped expanding end piece (6), wherein engagement faces for a dental gripping instrument are formed at the expanding end piece (6), wherein the expanding end piece (6) expands from a small diameter end which is connected to the end of the dental wedge disposed remote from the tip (2) to a larger diameter flat end face, wherein an axially aligned blind bore hole (9) is formed into the larger diameter flat end face of the expanding end piece (6), wherein the blind bore hole (9) serves for capturing the dental wedge with a dental gripping instrument.

13. The dental wedge according to claim 12, further comprising a cuboid shaped pedestal (7) joining into the larger diameter flat end face of the truncated cone shaped or truncated pyramidal shaped expanding end piece (6) and wherein the pedestal (7) is also penetrated by the blind bore hole (9).

14. The dental wedge according to claim 13, wherein at least one lateral face (8) of the pedestal (7) is arched concavely inwardly as a second engagement face for a dental gripping instrument.

15. The dental wedge according to claim 14, wherein the second engagement face is corrugated at the lateral face (8) of the pedestal (7).

16. The dental wedge according to claim 13, wherein indentations (10) are formed in at least two oppositely disposed lateral faces (8) as engagement faces for a dental gripping element.

17. The dental wedge according to claim 12, wherein the dental wedge (1) exhibits a first, longer wedge section (1a) and a second, shorter wedge section (1b) running out into a rounded, upwardly bent tip (2), wherein the impact edges (5) between the base face (3) and the side faces (4) in the first longer wedge section (1a) are running parallel to each other and the impact edges (5) only in the second wedge section (1b) run toward each other toward the free upwardly bent tip (2) of the dental wedge (1).

18. The dental wedge according to claim 12, wherein the impact edges (5) between the base face (3) and the side faces (4) of the dental wedge are sloped (21).

19. The dental wedge according to claim 12, wherein the base face (3) of the dental wedge (1) is furnished with a light reflecting structuring.

20. The dental wedge according to claim 12, wherein the base face (3) of the dental wedge (1) is furnished with a light reflecting structuring of the kind of a red reflex reflector.

* * * * *